United States Patent [19]
Schmidt et al.

[11] Patent Number: 5,989,842
[45] Date of Patent: Nov. 23, 1999

[54] METHOD OF MARKING BIOMOLECULES USING HORSERADISH PEROXIDASE

[75] Inventors: Eberhard Schmidt; Christa Weiss, both of Berlin, Germany

[73] Assignee: Bio-Tez Berlin-Buch GmbH, Germany

[21] Appl. No.: 09/105,163

[22] Filed: Jun. 26, 1998

Related U.S. Application Data

[63] Continuation of application No. PCT/DE96/02511, Dec. 24, 1996.

[30] Foreign Application Priority Data

Dec. 29, 1995 [DE] Germany .......................... 195 49 131

[51] Int. Cl.$^6$ .................................................. G01N 33/535
[52] U.S. Cl. .......................... 435/7.9; 435/188; 435/964; 436/544; 530/391.3; 530/391.5; 530/402
[58] Field of Search ............................... 530/345, 391.3, 530/391.5, 402; 435/7.9, 188, 964; 436/544

[56] References Cited

U.S. PATENT DOCUMENTS

| | | |
|---|---|---|
| 4,655,836 | 4/1987 | Mrawert et al. . |
| 4,657,853 | 4/1987 | Freytag et al. .......................... 435/188 |
| 5,057,313 | 10/1991 | Shih et al. . |
| 5,534,414 | 7/1996 | Pollner et al. .......................... 435/188 |

OTHER PUBLICATIONS

A.J. Pesce et al.: Preparation and Analysis of Peroxidase Antibody and Alkaline Phaophatase Antibody Conjugates, INSERM Symposium No. 2, North Holland Publ., 1976, pp. 7–23.

M.B.Wilson et al.: Recent Developments in the Periodate Method of Conjugating Horseradish Peroxidase to Antibodies, W. Knapp et al. Immunofluorscene & Related Statininf, Elsevier Press 1978, pp. 215–224.

P. K. Nakane et al.: Peroxidase–Labeled Antibody, J. Histochem. Cytochem, 22, 12, 1974, pp. 1084–1090.

K. Fujiwara: New Hapten–Protein Conjugation Method Using N(m–aminobenzyloxy) succinimide, etc., J. Immun. Methods, 175 (1994), Elsevier, pp. 123–129.

*Primary Examiner*—David Saunders
*Attorney, Agent, or Firm*—Schweitzer Cornman Gross & Bondell LLP

[57] ABSTRACT

The invention is a method for the enzymatic labeling of biomolecules, such as immunoglobulin, peptide, hormone, or hapten, which involves oxidizing horseradishperoxidase (HRP) with a periodate, crosslinking the oxidized HRP with an $\alpha,\Omega$-diaminoalkane, and coupling the biomolecule with the crosslinked, oxidized HRP.

11 Claims, No Drawings

METHOD OF MARKING BIOMOLECULES USING HORSERADISH PEROXIDASE

This is a continuation of international application No. PCT/DE96/02511, filed on Dec. 24, 1996.

FIELD OF THE INVENTION

The invention concerns a new method for the enzymatic labeling of antigens such as peptides, hormones or haptens and antibodies such as e.g. immunoglobulins of the IgG or IgM type which as enzyme tracers with an increased sensitivity are comparable to the sensitivity of radioactive tracers in radioimmunoassays (RIA) and can be used in enzyme immunoassays. Fields of application of enzyme immunological methods of detection include analytical determinations of a multitude of substances in blood, urea or liquor broadly applied in human and also veterinary medicine for research purposes, and, in particular, for practical clinical diagnostics. Their specificity and sensitivity depends, to a high degree, on the method of labeling by means of which the enzyme is crosslinked with the antigen or antibody.

BACKGROUND

Studies of enzyme immunoassay and related methods (EIA) show that a series of enzymes is known which are suited as markers (G. B. Wisdom: Clin. Chem. 22 (1976) 1242–1255; A. H. W, M. Schuurs, B. K. van Weemen (1977) in: Enzyme immunoassay, Grundlagen und Praktische Anwendung, Fundamentals and Practical Application), p. 4–9, Georg Thieme Verlag Stuttgart 1978; H. Keller: Medizine. Laboratorium 31 (1978), 83–94; T. Porstmann, S. T. Kiessig: J. Immunol. Methods 150 (1992) 5–21). However, to date horseradish peroxidase (HRP) is the choice enzyme because it is comparatively cheap, very pure and can be, therefore, produced with a high specific enzyme activity, and it is a "robust" biosubstance allowing chemical reactions without essentially loosing the reactivity of enzymes. For this reason, commercially available HPR conjugates are used in nearly 80% of all enzyme immunoassays. In the remaining approx. 20% mainly conjugates with an alkaline phosphatase are used. Only in special cases, labeling is effected with other enzymes such as e.g. β-galactosidase, glucose oxidase or acetylcholine esterase etc.

In preparing an enzyme conjugate the enzyme is crosslinked by a covalent bond with the immune substance to be labeled, without a reduction of neither the enzyme activity nor the immunoreactivity of the antigen or antibody. This presupposes that the two coupling partners have functional groups where appropriate coupling reagents can act directly or that reactive groups such as e.g. thiol or bismaleinimide groups are introduced and then in a second reaction step the conjugation is indirectly effected by homo- or heterobifunctional reagents (E. Ishkawa et al.: J. Immunoassay 4 (1983) 209–327). Already in the early 60 efforts have been made to produce HRP conjugates as markers for immunohistochemical examinations and as EIA tracers. According to the developments in this field at that time e.g. (i) 4,4'-difluoro 3,3'-dinitrophenyl sulfone (J. S. Ram: Biochim. Biophys. Acta 78 (1963) 228–230; P. K. Nakane, G. B. Pierce: J. Histochem. Cytochem. 14 (1966) 929), (ii) various carbodimides (S. Avrameas, J. Uriel: C. R. Acad. Sci. (D) Paris 262 (1966) 2543; P. K. Nakane, G. B. Pierce: J. Cell Biol. 33 (1967) 307–318), (iii) cyanuric chloride and bisdiazotized o-dianisidine (S. Avrameas: Bull. Chim. Biol. 50 (1968) 1169) etc. are used for the direct coupling of HRP and immunoglobulins (IgG). However, only IgG homopolymers are formed as main products of these so-called "one-pot processes", and most of the time not more than 5% of the HRP used will be obtained in the form of the desired HRP-IgG conjugate.

It was detected that the cause for this unexpected reaction behavior of HRP was that a molecule of the commercial horseradish peroxidase has only one to two reactive amino groups in spite of its comparatively high molecular weight of approx. 40 000. When isolating the enzyme from the plant by allyl isothiocyanate, forming of the substances ascorbic acid and sinigrin contained the majority of the originally available α- and ε-NH2 groups will be blocked. (L. Ornstein: J. Histochem. Cytochem. 14 (1966) 929; K. G. Welinder, L. B. Smillie, G. R. Schonbaum: Can. J. Biochem. 50 (1972) 44–62). In the direct crosslinking of HRP with immunoglobulins by glutaric dialdehyde described in 1969, which is carried out under mild reaction conditions through ε-amino groups of Lysine (S. Avrameas: Immunochemistry 6 (1969) 43) only about 5 to 10% coupling is obtained. Intensive self-crosslinking of the immunoglobulin takes place with high-molecular heterogeneous conjugates being formed (A. H. Korn, S. H. Feairheller, E. M. Filachione: J. Mole. Biol. 65 (1972) 525; D. H. Clyne, S. H. Norris, R. R. Modesto et al.: J. Histochem. Cytochem. 21 (1973) 233). Although it was found that the enzyme activity was essentially not affected, it was also found that when using this coupling method the immunoreactivity clearly declined (D. M. Boorsa, G. L. Kalsbeck: J. Histochem. Cytochem. 23 (1975) 200). Nevertheless, in the early 70 numerous HRP immunoconjugates were prepared for EIA purposes, primarily by this one-step glutaric aldehyde method.

In 1971 we succeeded in improving this one-step glutaric aldehyde coupling method (S. Avrameas, T. Ternynck: Immunochemistry 8 (1971) 1175–1179) after detecting that an HRP molecule is able to react only with one molecule of glutaric dialdehyde due to the small number of reactive amino groups even if the coupling reagent is available at an excess. The second aldehyde group cannot react with the same or another HRP molecule. This peculiar reaction behavior of HRP provides the basis for the so-called two-step coupling method in which the enzyme is first induced to react solely with glutaric dialdehyde. After separating the excess of the coupling reagent a monomeric HRP-glutaric dialdehyde coupling product is obtained, like some "activated peroxidase", which can react with the primary $NH_2$ groups of an antigen or antibody in a second reaction step in which preferably monomeric conjugates are formed (S. Avrameas: Histochem. J. 4 (1972) 321). Conjugates are also formed which contain 2 moles of enzyme per IgG molecule (D. M. Boorsma, J. G. Streefkerk: J. Immunol. Methods 30 (1979) 245–255). When applying this method of conjugation the reactivity of HRP is reduced by 30 to 50%, yet the loss of immunoreactivity is smaller than when applying the one-step method (T. J. Greenwalt, E. McF.Swierk, E. A. Steaner: J. Histochem. Cytochem. 21 (1973) 233), the efficiency of enzyme cross-linkage becomes insignificantly higher (N. Yamamoto: Acta Histochem. Cytochem. 8 (1975) 41). In spite of the aforementioned disadvantages a number of HRP conjugates were prepared as EIA tracers by this method (B. K. Weeman, A. H. W. M. Schuurs: FEBS Lett. 15 (1971) 232: Avrameas, B. Guilbert: Biochimie 54 (1972) 837).

The conditions for preparing the enzyme conjugates were still not satisfactory in the early 70 in spite of the use of enzyme immunological detection methods. This was the possible reason for Nakane and Kawoi developing a completely new strategy for preparing HRP-labeled antibodies in 1974. They proceeded on the basis that most of the enzymes were glycoproteins. In the case of horseradish peroxidase carbohydrates total approx. 18% of its molecular weight, and consist of 8 carbohydrate chains of known composition arranged on the surface of the enzyme, yet they are not related to the enzymatic activity of the molecule (L. Shannon, E. Kay, J. Y. Lew: J. Biol. Chem. 241 (1966) 2166–2172; K. G. Welinder, L. B. Smillie: Can. J. Biochem. 50 (1972) 63–90; K. G. Welinder: Eur. J. Biochem. 96 (1979) 483–509). If horseradish peroxidase is oxidized with sodium metaperiodate, the hydrocarbon residues are split with vicinal OH groups and aldehyde groups being formed without a significant loss of enzymatic activity (P. K. Nakane, A. Kawoi: J. Histochem. Cytochem. 22 (1974) 1084–1091). In this manner an "activated" HRP is formed which can directly react with primary $NH_2$ groups of an antigen or antibody, forming Schiff's bases. Subsequently, the unsaturated azomethine binding is appropriately stabilized by hydration with sodium borohydride. The HRP-labeled tracer is separated in a manner known per se by gel filtration or dialysis.

The coupling method adopted by Nakane avoids difficulties that could occur in earlier conjugation methods due to the fact that an HRP molecule has only one 50th or even fewer reactive primary amino groups which can be affected by the coupling reagents compared to an IgG molecule. As no IgG self-crosslinking will take place, the coupling efficiency is high: it totals approx. 70% as to HRP, and 90–95% as to IgG. When applying this method neither the enzyme activity nor the immunoreactivity are fully maintained. The corresponding data in literature vary, they closely depend from the reaction conditions of the sodium metaperiodate oxidation and the reduction with $NaBH_4$. As the oxidized HRP molecule has a bigger number of glucose hemiglutaryl linkers on its surface, it is in a position to conjugate not only with one, but with several IgG molecules. Depending on the stoichiometric ratio the oxidized HRP and IgG are converted to form crosslinked aggregates of a molecular weight of 400 000 and more. The few primary amino groups still available in the HRP molecule were blocked with 1-fluoro-2,4-dinitrobenzene before the $NaIO_4$ oxidation took place to exclude crosslinking of HRP molecules.

After detailed examination of the effect of individual stages of the $NaIO_4$ coupling on the enzymatic and the immunological properties of the HRP IgG conjugates, Wilson and Nakane published an improved method in 1978 which formed the basis for peroxidase labeling until today (B. Wilson, P. K. Nakane: Recent Developments in the Periodate Method of Conjugating Horseradish Peroxidase to Antibodies, Immunofluorescence and Related Staining Techniques (Eds.: W. Knapp, K. Holubar, G. Wick), pp. 215–224, Elsevier: North-Holland Biomedical Press 1978). Blocking of the primary $NH_2$ groups with 1-fluoro-2,4-dinitrobenzene was considered essential before the $NaIO_4$ oxidation was stopped. In spite of this precaution self-crosslinking of the oxidized HRP could not be completely suppressed as the protective blocking had to take place in an alkaline buffer solution, and sodium metaperiodate is partly inactivated in an alkaline medium. Therefore, oxidation of HRP is suitably conducted in a neutral or weak acetic acid solution. For that reason the periodate excess is separated by dialysis or gel filtration at a pH between 4 and 5. Even if the HRP activated by the formed aldehyde groups is stored for a short time, self-conjugation will remain under 5% at this low pH. Optimum reaction conditions prevail if the 1st stage of the Wilson-Nakane coupling method, the oxidation of HRP, is carried out in the dark at a $NaIO_4$ concentration of 0.02 M at room temperature, and a 200 times molar peroxidase excess of 200. Thus, a photochemical oxidation of the hydrocarbon residues by ozone formed during photodecomposition of $NaIO_4$ is avoided (E. B. Dikova, E. M. Gavrilova, A. M. Yegorov: Bioorgan. Khim. (Moscow) 16 (1990) 476–481). A sufficient reaction time is 20 minutes; there are groups which reduce it even to 10 minutes (M. Imagawa, S. Yoshitake, Y. Hamaguchi et al.: J. appl. Biochemistry 4 (1982) 41–57). Wilson and Nakane mention that an HRP molecule oxidized in this manner with $NaIO_4$ has at least 18 reactive aldehyde catcher groups at its surface, however, not all of them can be used for coupling with IgG molecules, presumably for steric reasons. The 2nd stage of the coupling, the conjugation of the oxidized HRP with immunoglobulin or other proteins which are to be labeled by horseradish peroxidase, is carried out in a solution buffered by bicarbonate at pH>9, optimally between 9.5 and 9.8 while forming Schiff's bases. Wilson and Nakane point out that the coupling time should not be less than 2 hours at room temperature. More favorably the reaction is to be allowed to take place within 4 hours at room temperature. Multi-component mixtures of oligomeres of a differing molecular mass are formed here depending on the stoichiometric ratio of the reactants. If a clear excess of oxidized HRP is used, 5–6 HRP molecules can be bound to an IgG molecule without steric hindrance. The formation of polymeric conjugates is unavoidable since an oxidized HRP molecule can react again with more than one IgG molecule by its aldehyde groups. A model describing this complex reaction process is in good agreement with the experimental results obtained by Wilson and Nakane was prepared by Archer (P. G. Archer: Biometrics 32 (1976) 369–375). Under higher reaction conditions the experimental values are below the values calculated according to the model. They are also disturbing by a high error rate in the spectrophotometric determination of the peroxidase share of a conjugate measured at 403 nm, and of its total protein content resulting from the extinction at 280 nm.

The 3rd stage of the Wilson-Nakane coupling method, the hydration with sodium borohydride, is beyond any doubt a critical stage which requires stabilization of the unsaturated azomethine bonds of the Schiff's bases and also the conversion of the excessive aldehyde groups into the respective carbinols through reduction. This reaction is effected immediately after coupling. It is carried out in a solution buffered by bicarbonate at pH 9.5 at 4° C., with $NaBH_4$ used in a molar excess of 100 times the HRP that is used. The reaction time should be not less than 2 hours. Though $NaBH_4$ is a selective reducing agent, various groups mentioned that its use results in a remarkable loss of enzyme activity which can total 18% and more. For this reason, Pierce, a U.S. company recommends to dispense with the stabilization of the azomethine bonds and to quench only the excessive aldehyde groups with Lysine or ethanolamine (Pierce Immuno-Technology Catalog & Handbook 1992) or to use the less strong reactant sodium cyanoborohydride instead of $NaBH_4$ to show a better compatibility also as compared to IgG (Pierce Seminar 5: Antibody-Enzyme Conjugates, Methods for Preparation and Purification 1993).

The last stage of the Wilson-Nakane coupling method is the isolation of the high-molecular conjugate of the coupling mixture. The separation of the low-molecular coupling products, the starting protein not labeled by HRP and the free enzyme, is an essential step in obtaining a HRP tracer with optimum properties resulting in a remarkable increase of the sensitivity of the assay. This separation task cannot be completed by dialysis or gel filtration, and separation of the tracer in an exclusion volume of a column filled with Sephadex G-25, but rather by gel permeation chromatography through a Sephacryl-S-300® column (Pharmacia) which is eluted with 0.05 M of PBS buffer (0.15 M of NaCl) at pH 7.4.

In summary, the preparation of a HRP-IgG conjugate according to the Wilson-Nakane method will result in a high-molecular complex where the immunoglobulin molecule represents something like the core which can bind as many HRP molecules on its surface through its activated aldehyde groups as the steric conditions will allow. Presumably, the HRP molecules will be crosslinked among each other only to a minor extent. Sensitive tracers used for an EIA require, however, that the degree of HRP substitution be not less than 2, but it should be clearly higher. Yet, with an increasing degree of substitution the surface of the central immunoglobulin will be increasingly screened off. This is a possible, at least partial explanation for the decline of the observed immunoreactivity. Also the spectrophotometrically obtained faulty total protein content values at 280 nm, can be caused due to the described structure of the HRP conjugate.

DESCRIPTION OF THE INVENTION

It is an object of the present invention to provide an improvement in the method of labeling biomolecules with horseradish peroxidase of Wilson and Nakane, to obtain structurally modified HRP protein conjugates in which neither enzymatic areas nor bonding positions of the total molecule responsible for the immunoreactivity affect each other due to steric inhibition. This should also salutarily affect the results of the spectrophotometric measurement of produced on each HRP molecule which cannot be used in the subsequent direct coupling of a larger protein molecule as e.g. of IgG. The structuring of such a HRP network depends on the length of the bifunctional spacer used and the stoichiometric ratio in which it is induced to react with the oxidized horseradish peroxidase.

It was experimentally found out that 1,6-diamino-hexane (hexamethylene diamine or HMD) is particularly suited for crosslinking, as a solid, readily water-soluble substance. Shorter diaminoalkanes such as ptomaine putrescine (1,4-diaminobutane), and cadaverine (1,5-diaminopentane) are liquid at room temperature and particularly due to their unpleasant smell are less suited. Longer diaminoalkanes of up to 1,9-diaminononane can also be used for crosslinking horseradish peroxidase, yet do not provide an advantage. When using 1,10-diaminodecane (decamethylene diamine, DMD) the fact that its water-insolubility increases with increasing chain length, is disturbing. In coupling carried out with HRP crosslinked with DMD conjugates the properties obtained proved to be less good in EIA as compared with conjugates where HRP is crosslinked with HMD.

$\alpha,\Omega$-diaminoalkanes the chain of which contains a few oxa-bridges are especially well suited for the crosslinking of peroxidase. Such compounds are liquids which can be mixed with water to an unlimited extent. In this way the length of the spacer can be increased, with the HRP network being loosened without affecting its water-solubility. 1,13-diamino-4,7,10 trioxatridecane (DTT) that has become commercially available only recently, shows very favorable properties for the peroxidase crosslinkage. The $\alpha,\Omega$-diaminoalkanes suited for the peroxidase crosslinking include

| | | |
|---|---|---|
| H2N—CH2—CH2—CH2—CH2—CH2—CH2—NH2 | | |
| 1,6-diaminohexane | C6H16N2 | 166.2078 |
| H2N—CH2—CH2—CH2—CH2—CH2—CH2—CH2—NH2 | | |
| 1,7-diaminoheptane | C7H18N2 | 130.2349 |
| H2N—CH2—CH2—CH2—CH2—CH2—CH2—CH2—CH2—NH2 | | |
| 1,8-diaminooctane | C8H20N2 | 144.2620 |
| H2N—CH2—CH2—CH2—CH2—CH2—CH2—CH2—CH2—CH2—NH2 | | |
| 1,9-diaminononane | C9H22N2 | 158.2891 |
| H2N—CH2—CH2—O—CH2—CH2—O—CH2—CH2—NH2 | | |
| 1,8 diamino-3,6-oxaoctane | C6H16N2O2 | 148.2066 |
| H2N—CH2—CH2—CH2—O—CH2—CH2—CH2—CH2—O—CH2—CH2—CH2—NH2 | | |
| 1,12-diamino-4,9-dioxadodecane | C10H24N2O2 | 204.3150 |
| H2N—CH2—CH2—CH2—O—CH2—CH2—O—CH2—CH2—O—CH2—CH2—CH2—NH2 | | |
| 1,13-diamino-4,7,10-trioxatridecane | C10H24N2O3 | 220.3144 | the majority of the HRP conjugates that are prepared, in that in addition to the extinction that is normally determinable at 402 nm for the enzyme, a determination can also be made at 278 nm which indicates the total protein content, thus allowing a more reliable analytical calculation.

The invention creates a new method of enzymatic labeling of biomolecules of various types, most suitably of immunoglobulins, based on the method of Wilson and Nakane, which allows production of HRP tracers with a test sensitivity that has so far only been reached in RIA. It is also an object to eliminate the problems of spectrophotometric measurement that so far restricted analytical characterization of the preparations.

The method of the present invention first oxidizes HRP with a periodate, and then crosslinks the HRP (ox.) molecules with an $\alpha,\Omega$-diaminoalkane. The oxidation itself is carried out in conformity with the data of Wilson and Nakane where such a large number of aldehyde groups is Crosslinking is suitably carried out by consuming only a small part of the aldehyde groups formed during oxidation with periodate. One should not choose more than a molar HMD or better DTT excess by 2.5 up to 3.5 times related to the amount of the HRP. One then obtains a high-molecular HRP conjugate with an extremely high enzymatic activity. However, with the growth of the molecule brought about by crosslinking, also the nonspecific bonding of such a HRP tracer in the EIA will grow. To keep it within reasonable limits it is more favorable to react the $\alpha,\Omega$-diaminoalkane only in a molar excess of 0.5 to 1.5 times for crosslinking with HRP. When using more HDM or DTT than a molar excess of 3.5 times, the protein that is not coupled to the HRP network increases and the yield of HRP conjugate declines.

Suitably a 0.002 M of HMD or DTT solution in 0.1 M of bicarbonate buffer (pH 9.8) is prepared for crosslinking. This solution can be stored also for later use. 75 µl of this solution are added to the HRP (ox.) solution obtained by the oxidation of 4 mg native horseradish peroxidase with periodate in 0.005 M of acetate buffer (pH 4.3), and concentrated by ultrafiltration to a volume of approx. 0.2 ml. 4 hours of reaction time is required at room temperature for crosslinking; it can also be effected overnight in a refrigerator at 40° C.

Thus, an aggregate is produced of 6 to 10 HRP molecules where through the aldehyde groups one or a few immunoglobulin molecules or also other proteins can be covalently bonded without prior separation from the reaction mixture. This is implemented in practice by adding the protein dissolved in 0.1 M of bicarbonate buffer (pH 9.8) to the crosslinked HRP solution or vice versa. The reaction conditions are the same as in the case of crosslinking, i.e. the reaction is merely continued. In this way, a substantially higher degree of substitution can be obtained. As the IgG molecule is not screened off by HRP molecules it can fully develop its immunological properties and can be correctly measured by spectrophotometry. Of course, unsaturated azomethine bonds have to be stabilized by hydration with sodium borohydride or sodium cyanoborohydride. Optimal properties can be obtained if the HRP-labeled tracer is separated by gel permeation chromatography through Sephacryl S-300 which enables separation of the low-molecular coupling products contained in the reaction mixture, possibly also of uncoupled protein and also of not crosslinked, i.e. free HRP.

In its entirety, the new HRP-labeling method of the present invention represents remarkable progress in the development of efficient enzyme immunological detection systems. After oxidation with sodium periodate, the present invention presents a purposeful crosslinking of the horseradish peroxidase with an α,Ω-diaminoalkane, suitably with 1,13-diamino-4,7,10-trioxa-tridecane before coupling with the protein to be labeled, instead of an uncontrolled formation of heterogenous coupling products, as in the prior art. Thus, a high degree of substitution can be obtained without essentially changing the enzymatic and, particularly, the immunological properties. The sensitivity and specificity of the HRP tracer that is then obtained is extraordinarily high and, is entirely comparable with radio tracers. Their analytical characterization on the basis of spectrometric measurements provides reliable values if the extinction measured for the protein at 280 nm will be corrected by considering the extinction at this wavelength depending on concentration.

The following examples further illustrate the present invention.

The following 5 steps of preparation are carried out in labeling an immunoglobulin (IgG) with horseradish peroxidase (HRP):

(i) oxidation of HRP with $NaIO_4$;
(ii) crosslinking of HRP (ox.) with 1,13-diamino-4,7,10-troxatridecane (DTT);
(iii) coupling of IgG with crosslinked HRP;
(iv) stabilization of the azomethine bonds; and
(v) S-300 gel permeation chromatography.

Steps (ii) and (iii) are carried out in connection with the method of the present invention. They are described in detail by the example of the HRP—labeling of IgG (rabbits) with 1,13-diamino-4,7,10-trioxatridecane. Therefore, steps (i), (iv) and (v) which are only indirectly connected with the present invention and are generally known, are described here only briefly.

(i) Oxidation of HRP with $NaIO_4$ 4.0 mg of horseradish peroxidase (HRP, 100 nmole) are weighed in a reaction tube, dissolved in 0.8 ml of water and 0.2 ml of freshly prepared 0.1 M of $NaIO_4$ solution is pipetted into the copper-red HRP solution, the color of which changes to black-green. The reaction tube is placed immediately into an enclosure which is closed to avoid exposure to light. The reaction time totals 15 min. at room temperature, with an occasional moving of the tube.

50 μl of ethylene glycol are added to avoid an excess of $NaIO_4$. This quenching is also carried out in the dark and the reaction time totals at least 30 min. Thereupon, the HRP (ox.) solution again becomes copper-red. The separation of HRP (ox.) from low-molecular reactants is effected by gel filtration in the exclusion volume of a Sephadex-G 25 column (approx. 30 cm long, 12 ml of gel bed volume). It is sufficient to take 20 fractions per 0.5 ml. The red-brown HRP containing fractions are pooled and are evaporated by ultrafiltration (10,000 NMGG) to a volume ≦ 0.5 ml.

(ii) HRP (ox.) Cross-linking with DTT in the Event of an Equimolar Batch 10 ml of DTT (δ=1.005) are pipetted into a 50 ml measuring flask, that is filled to the mark with 0.1 M bicarbonate buffer (pH 9.8). This DTT solution can be used for more than 2 months.

0.1 ml (100 nmole) of this solution are pipetted into the HRP (ox.) solution concentrated by evaporation. A microstirrer is inserted to mix the reaction solution rapidly and thoroughly. The reaction time for crosslinking totals 4 hours at room temperature; if needed, the reaction mixture may also be placed into a refrigerator overnight.

(iii) IgG Coupling with Crosslinked HRP

The stoichiometric ratio between crosslinked HRP and IgG should suitably be about 5:1 to obtain a high degree of substitution. 15 to 16.7 nmole are used for coupling in view of an insignificant loss of HRP in the 1st and 2nd preparation stages 2.25 to 2.50 mg of IgG (rabbits). Immunoglobulin is either directly inserted into the reaction tube which contains the crosslinked HRP solution in 0.1 M bicarbonate buffer (pH 9.8), and dissolved by stirring, or is earlier dissolved in 0.1 M bicarbonate buffer (pH 9.8), and is then added. During IgG coupling the reaction conditions are the same as during crosslinking reaction at room temperature either for 4 hours or the coupling mixture is placed into a refrigerator overnight. The reaction volume should not exceed 0.8 ml.

(iv) Stabilization of the Azomethine Bonds

50 μl 2 M of triethanolamine (pH 8.0) are added to the coupling solution, the reaction mixture is thoroughly mixed and cooled in a refrigerator. 0.2 M of $NaBH_4$ solution are prepared for hydration of the azomethine bonds, with 8 mg $NaBH_4$ dissolved in 1.0 ml cold water only immediately before being used. Not more than 75 μl of this solution are added to the coupling solution. When stirring it the reaction solution foams vehemently. The reaction time totals approx. 30 min. in the refrigerator before 25 μl 2 M of triethanolamine (pH 8.0) are added. The reaction mixture is placed into a refrigerator for another 2 hours. Finally, still 10 μl 1 M of glycine (pH 7.0) are added for stabilization.

(v) S-300 Gel Permeation Chromatography

The HRP tracer is separated in a 75 cm long Sephacryl-S 300® column (approx. 41 ml of gel bed volume) which is eluted with 0.05 M of PBS buffer/0.15 M of NaCl (pH 7.4). 35–40 fractions of 1.0 ml each are taken off. Only the fractions with high extinctions at 402 nm showing the most favorable properties as to their specific and nonspecific bonds in EIA, at most only 3 tubes, are pooled.

We claim:

1. A method for the enzymatic labeling of biomolecules, which comprises oxidizing horseradishperoxidase (HRP) with a periodate, crosslinking the oxidized HRP with an α,Ω-diaminooxaalkane, and coupling the biomolecule with the crosslinked, oxidized HRP.

2. The method of claim 1, wherein said biomolecule is an immunoglobulin, peptide, hormone, or hapten.

3. The method of claim 1, wherein said periodate is sodium periodate.

4. The method of claim 1, wherein said α,Ω-diaminooxaalkane is a water miscible liquid at room temperature.

5. A The method of claim 1, wherein said α,Ω-diaminooxaalkane is 1,8 diamino-3,6-oxaoctane, 1,12-diamino-4,9-dioxadodecane, or 1,13-diamino-4,7,10-trioxatridecane.

6. The method of claim 1, wherein said α,Ω-diaminooxaalkane is used at a molar excess of 3.5 times related to the oxidized HRP.

7. The method of claim 1, wherein said α,Ω-diaminooxaalkane is used at a molar excess of from 0.5 to 1.5 times related to the oxidized HRP.

8. The method of claim 1, wherein after said step of oxidizing any surplus of periodate is quenched with ethylene glycol.

9. The method of claim 6, further comprising separating the oxidized HRP from low molecular weight reactants by gel filtration on Sephadex G-25.

10. The method of claim 1, wherein said coupling is carried out in a solution buffered by bicarbonate at pH>9.

11. The method of claim 1, wherein said coupling takes place at a pH of 9.8.

* * * * *